United States Patent
Kitching et al.

(10) Patent No.: US 8,038,444 B2
(45) Date of Patent: Oct. 18, 2011

(54) AUTOMATED TREATMENT STAGING FOR TEETH

(75) Inventors: Ian Kitching, San Jose, CA (US); Alexander Dmitriev, Moscow (RU); Alexey Vishnevskiy, Moscow (RU)

(73) Assignee: Align Technology, Inc., San Jose, CA (US)

( * ) Notice: Subject to any disclaimer, the term of this patent is extended or adjusted under 35 U.S.C. 154(b) by 1070 days.

(21) Appl. No.: 11/848,172

(22) Filed: Aug. 30, 2007

(65) Prior Publication Data
US 2008/0057462 A1 Mar. 6, 2008

Related U.S. Application Data

(60) Provisional application No. 60/824,022, filed on Aug. 30, 2006, provisional application No. 60/824,024, filed on Aug. 30, 2006.

(51) Int. Cl.
*A61C 3/00* (2006.01)

(52) U.S. Cl. .......................................... 433/213; 433/24

(58) Field of Classification Search .................... 433/24, 433/213
See application file for complete search history.

(56) References Cited

U.S. PATENT DOCUMENTS

| | | | |
|---|---|---|---|
| 6,217,325 B1 * | 4/2001 | Chishti et al. ................ | 433/24 |
| 6,409,504 B1 | 6/2002 | Jones et al. | |
| 6,471,511 B1 | 10/2002 | Cheshti et al. | |
| 6,514,074 B1 | 2/2003 | Cheshti et al. | |
| 6,729,876 B2 * | 5/2004 | Chishti et al. ................ | 433/24 |
| 7,063,532 B1 | 6/2006 | Jones et al. | |
| 7,331,783 B2 * | 2/2008 | Chishti et al. ................ | 433/24 |
| 7,377,778 B2 * | 5/2008 | Chishti et al. ................ | 433/24 |
| 7,435,083 B2 * | 10/2008 | Chishti et al. ................ | 433/24 |
| 7,578,674 B2 * | 8/2009 | Chishti et al. ................ | 433/24 |
| 7,637,740 B2 * | 12/2009 | Knopp ........................ | 433/24 |
| 7,658,610 B2 * | 2/2010 | Knopp ........................ | 433/24 |
| 7,819,659 B2 * | 10/2010 | Wen ........................... | 433/6 |
| 7,844,356 B2 * | 11/2010 | Matov et al. ............... | 700/98 |
| 7,844,429 B2 * | 11/2010 | Matov et al. ............... | 703/7 |
| 7,904,307 B2 * | 3/2011 | Abolfathi et al. ........... | 705/2 |
| 2006/0275736 A1 * | 12/2006 | Wen et al. .................. | 433/213 |

OTHER PUBLICATIONS

Muhammad Chishti et al., abandoned U.S. Appl. No. 09/169,276, filed Oct. 8, 1998.

* cited by examiner

*Primary Examiner* — David A Vanore
(74) *Attorney, Agent, or Firm* — Kilpatrick Townsend & Stockton LLP

(57) ABSTRACT

Apparatus, system, and methods for utilizing one or more computing devices to stage the movement of teeth during an alignment treatment are disclosed. The computing device receives an electronic representation of the patient's teeth in their initial position and an electronic representation of the teeth a final position for each tooth. A route each tooth will travel to reach its final position is determined, and the teeth are scheduled to move according to a movement pattern. Moreover, the schedule of movement takes into account a maximum rate of tooth movement for each tooth, the path of movement for each tooth, the distance each tooth needs to move, any needed tooth staggering, any needed round-tripping or tooth movement slowing. The invention also includes techniques for determining an optimum number of stages for the treatment based on the schedule of movement.

42 Claims, 15 Drawing Sheets

| Stg | 7(2) | 6(3) | 5(4) | 4(5) | 3(6) | 2(7) | 1(8) | 1(9) | 2(10) | 3(11) | 4(12) | 5(13) | 6(14) | 7(15) | 8(16) |
|---|---|---|---|---|---|---|---|---|---|---|---|---|---|---|---|
| 8 |  | .29 | .29 | .23 | .27 |  |  |  |  |  |  | .17 | .15 |  |  |
| 9 |  |  | .30 | .23 | .27 |  |  |  |  |  |  | .17 | .15 |  |  |
| 10 |  |  | .30 | .23 | .27 |  |  |  |  |  | .31 | .17 | .14 |  |  |
| 11 |  |  |  | .23 | .27 |  |  |  |  |  | .30 | .17 | .14 |  |  |
| 12 |  |  |  | .23 | .27 | .23 | .22 | .09 | .24 |  | .30 | .17 |  |  |  |
| 13 |  |  |  |  | .28 | .23 | .22 | .09 | .24 |  | .30 | .17 |  |  |  |
| 14 |  |  |  |  | .28 | .23 | .23 | .10 | .24 |  | .30 |  |  |  |  |
| 15 |  |  |  |  | .28 | .23 | .23 | .10 | .24 |  | .30 |  |  |  |  |
| 16 |  |  |  |  | .28 | .23 | .23 | .10 | .24 |  | .30 |  |  |  |  |
| 17 |  |  |  |  |  | .23 | .23 | .10 | .24 |  |  |  |  |  |  |
| 18 |  |  |  |  |  | .23 | .23 | .10 | .24 |  |  |  |  |  |  |
| 19 |  |  |  |  |  | .23 | .23 | .10 | .24 |  |  |  |  |  |  |
| 20 |  |  |  |  |  | .23 | .23 | .10 | .24 |  |  |  |  |  |  |
| 21 |  |  |  |  |  | .23 | .23 | .10 | .24 |  |  |  |  |  |  |
| 22 |  |  |  |  |  | .16 | .23 | .10 | .18 |  |  |  |  |  |  |
| 23 |  |  |  |  |  | .16 | .23 | .10 | .18 |  |  |  |  |  |  |
| 24 |  |  |  |  |  | .16 | .24 | .10 | .18 |  |  |  |  |  |  |
| 25 |  |  |  |  |  | .16 | .24 | .10 | .18 |  |  |  |  |  |  |
| 26 |  |  |  |  |  | .16 | .24 | .10 | .18 |  |  |  |  |  |  |
| 27 |  |  |  |  |  | .16 | .24 | .10 | .18 |  |  |  |  |  |  |
| 28 |  |  |  |  |  | .15 | .24 |  |  |  |  |  |  |  |  |
| 29 |  |  |  |  |  | .15 | .24 |  |  |  |  |  |  |  |  |
| 30 |  |  |  |  |  | .15 | .24 |  |  |  |  |  |  |  |  |
| 31 |  |  |  |  |  | .15 | .24 |  |  |  |  |  |  |  |  |
| 32 |  |  |  |  |  | .21 | .12 |  |  |  |  |  |  |  |  |
| 33 |  |  |  |  |  | .21 | .12 |  |  |  |  |  |  |  |  |

Key Frame | Move Dist | Collision | Space | Overcorrection | Translation (mm) | Rotation (deg)

FIG. 10B

AUTOMATED TREATMENT STAGING FOR TEETH

CROSS REFERENCE TO RELATED APPLICATIONS

This application claims the benefit and priority of U.S. Provisional Patent Application No. 60/824,022, filed Aug. 30, 2006, and U.S. Provisional Patent Application No. 60/824,024, filed Aug. 30, 2006, both of which are herein incorporated by reference.

BACKGROUND

1. Field of the Invention

The present invention is related generally to the field of orthodontics, and more particularly to staging a path of movement for correcting the position of one or more teeth.

2. Related Art

One objective of orthodontics is to move a patient's teeth to positions where the teeth function optimally and aesthetically. Conventionally, braces are applied to the teeth of a patient by an orthodontist. The braces exert continual force on the teeth and gradually urge the teeth to their respective ideal position. The orthodontist does this by adjusting the braces position over time to move the teeth toward their final destination.

Apparatus, systems, and methods have been developed to facilitate teeth movement utilizing clear, removable teeth aligners as an alternative to braces. A mold of the patient's bite is initially taken and desired ending positions for the patient's teeth (i.e., a functionally and aesthetically optimum position) are determined, based on a prescription provided by an orthodontist or dentist. Corrective paths between the initial positions of the teeth and their desired ending positions are then planned. These corrective paths generally include a plurality of intermediate positions between the initial and ending positions of the teeth. Multiple clear, removable aligners formed to move the teeth, to the various positions along the corrective path are then manufactured. One system for providing such aligners formed to move the teeth to the various positions along the corrective path is the Invisalign® System from Align Technologies Inc. of Santa Clara, Calif.

In currently available systems for providing clear, removable tooth aligners, it is often necessary to manually manipulate digital and/or physical models of a patient's teeth to plan movements of the teeth through their various treatment stages, and, thus, to manufacture the corresponding stages of aligners. Although some aspects of the planning and manufacturing processes have been automated, one continuing technical challenge has been to further automate these processes. This challenge is difficult to overcome, primarily because every patient's teeth are unique and their movements during treatment are also unique. In a tooth moving treatment involving multiple clear, removable aligners, every aligner made is different from every other aligner, not only for one patient but, of course, from patient to patient as well. Therefore, automating treatment planning and aligner manufacturing is extremely challenging. At the same time, manually planning each stage of treatment is quite labor and time intensive and requires extensive training.

Therefore a need clearly exists for apparatus, systems, and methods to increase automation of a tooth movement treatment planning process. Ideally, such automation would reduce the time and resources needed to stage the movement of teeth during an alignment treatment. At least some of these objectives will be met by the present invention.

SUMMARY

Embodiments of the present invention provide apparatus, systems, and methods for automated staging of teeth, from an initial position to a final, corrected position. Depending upon the particular needs of the patient, the patient's teeth are scheduled to move according to various movement patterns, routes, rates, and/or distances; and the need for utilizing tooth staggering, round-tripping, and/or slowing techniques. Furthermore, the invention provides techniques for minimizing the treatment period of the patient based upon the pattern, route, rate, and/or distance selected for the patient's individual needs, as well as the need for any tooth staggering, round-tripping and/or slowing technique(s).

BRIEF DESCRIPTION OF THE DRAWINGS

A more complete understanding of the present invention may be derived by referring to the detailed description and claims when considered in connection with the drawing Figures, where like reference numbers refer to similar elements throughout the Figures, and:

FIG. 10B is a diagram of the exemplary embodiment of FIG. 5 utilizing different rates of movement to avoid collisions with and/or obstructions between teeth during the orthodontic treatment.

DETAILED DESCRIPTION OF THE INVENTION

U.S. patent application Ser. No. 09/169,276, now abandoned; Ser. Nos. 09/264,547; and 09/311,716, now U.S. Pat. No. 6,514,074 describe techniques for generating 3-dimensional digital data sets containing models of individual components of a patient's dentition. These data sets include digital models of individual teeth and the gingival tissue surrounding the teeth. Furthermore, these applications also describe computer-implemented techniques for using the digital models in designing and simulating an orthodontic treatment plan for the patient. For example, one such technique involves receiving an initial data set that represents the patient's teeth before treatment, specifying a desired arrangement of the patient's teeth after treatment, and calculating transformations that will move the teeth from the initial to the final positions over desired treatment paths. U.S. patent application Ser. No. 09/169,276 also describes the creation of data sets representing the tooth positions at various treatment stages and the use of these data sets to produce orthodontic appliances that implement the treatment plan. One technique for producing an orthodontic appliance involves creating a positive mold of the patient's dentition at one of the treatment stages and using a conventional pressure molding technique to form the appliance around the positive mold. A design of orthodontic appliances from the digital dentition models is, for example, described in U.S. patent application Ser. No. 09/169,034.

Figure 1A:
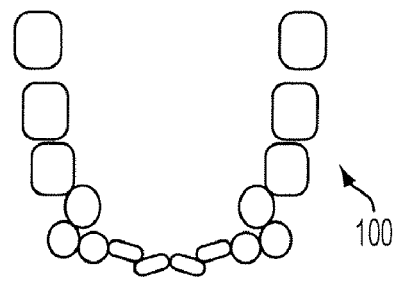
FIGS. 1A, 1B, and 1C are diagrams showing the arrangement of a patient's teeth at an initial stage, an intermediate stage, and a final stage, respectively, of orthodontic treatment.
Figure 1B:
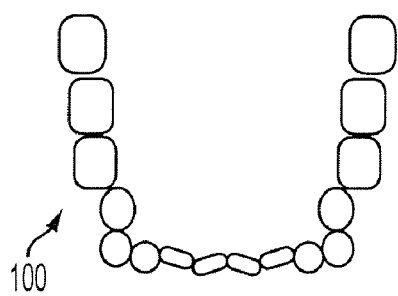
Figure 1C:
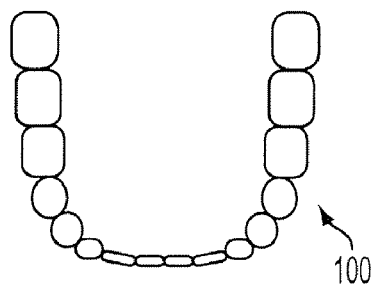

FIGS. 1A, 1B, and 1C show a patient's dentition at three stages during a course of treatment. FIG. 1A illustrates the initial positions of the patient's teeth before treatment begins. A digital model of the teeth at these initial positions is captured in an initial digital data set (IDDS). The digital model contained in the IDDS also includes portions representing gingival tissue surrounding the patient's teeth. A computer program segments the IDDS into digital models of individual teeth and the gingival tissue.

FIG. 1B illustrates an example of how the patient's teeth may be oriented at an intermediate stage in the treatment process, and FIG. 1C illustrates an example of how the patient's teeth may be oriented at their final positions. A human operator and/or a computer program manipulate the digital models of the patient's teeth to achieve the final tooth positions. The program then calculates one or more of the intermediate positions, taking into account any constraints imposed on the movement of the teeth by the human operator or by the natural characteristics of the teeth themselves. The program also accounts for any collisions that might occur between teeth as the teeth move from one treatment stage to the next. Selecting the final and intermediate tooth positions and the treatment paths along which the teeth move is described in more detail in one or more of the Patent Applications discussed above, which are all hereby incorporated by reference, in their respective entireties.

Figure 1D:
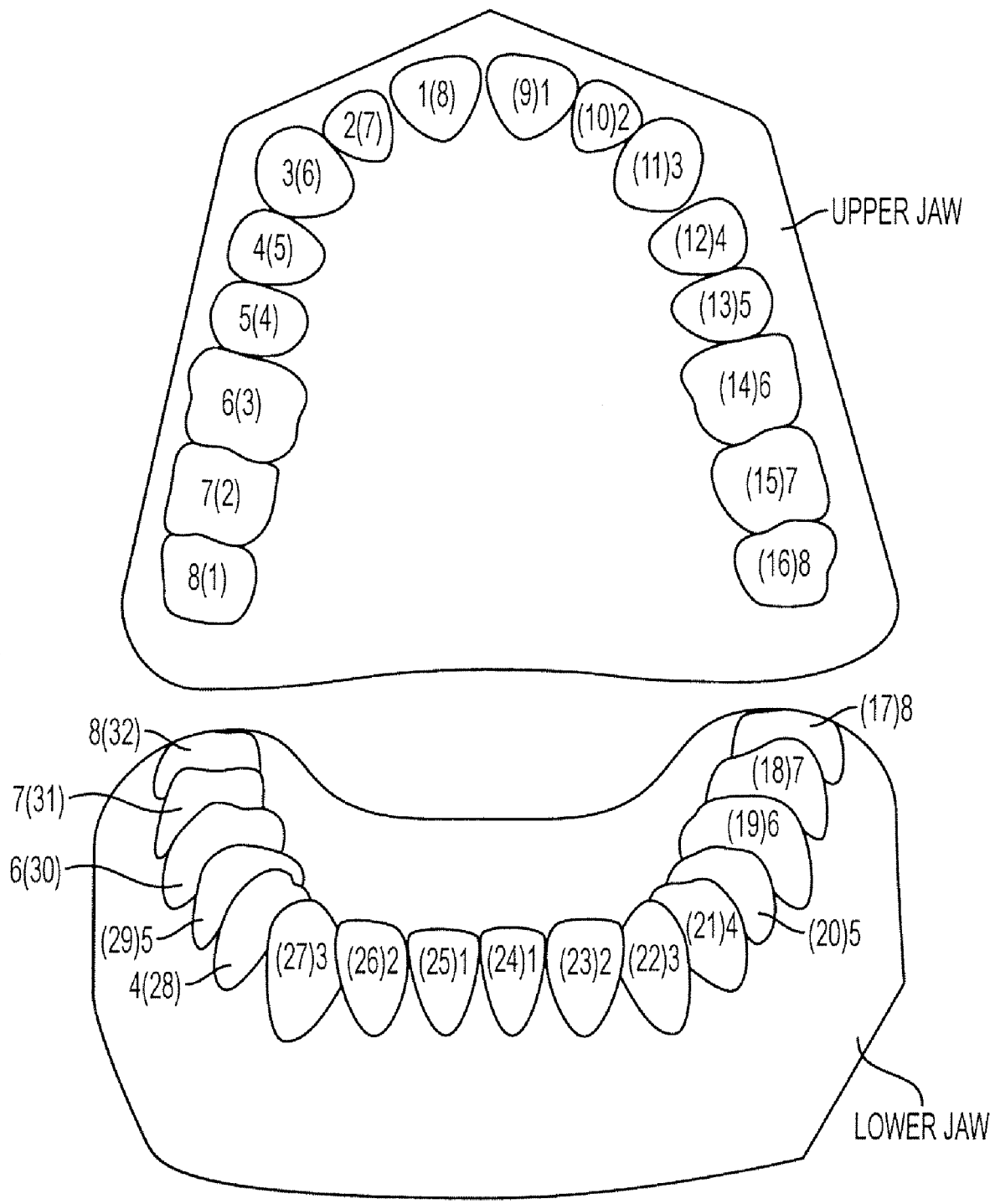
FIG. 1D is a diagram showing teeth numbering according to the standard system of tooth numbering.

FIG. 1D is a diagram of a set of teeth showing the standard system of numbering teeth. Reference is made to this standard system of numbering throughout the discussion below.

Figure 2A:
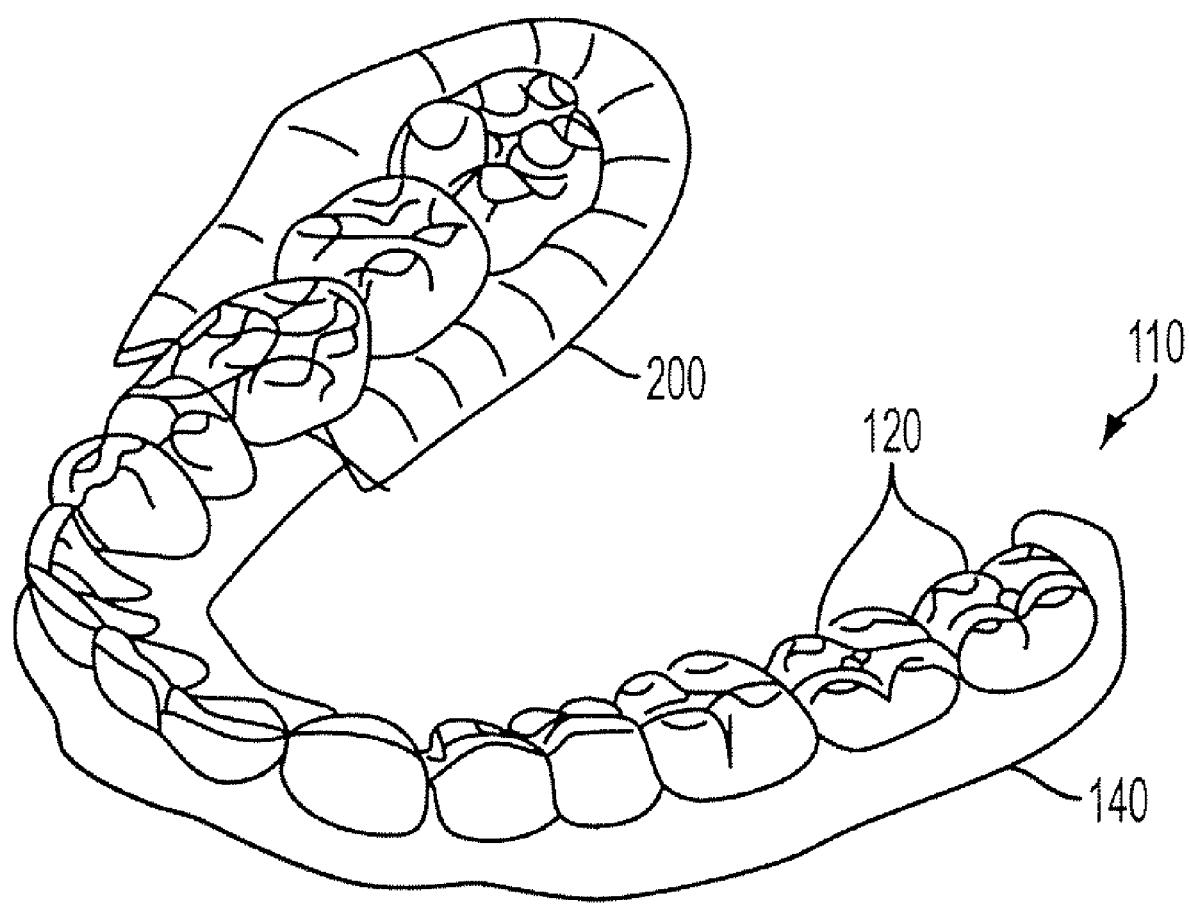
FIG. 2A is a diagram illustrating a partial model of a patient's dentition, including a model of gingival tissue.

FIG. 2A is a diagram illustrating a portion of a typical digital dentition model 110 derived from the IDDS. Dentition model 110 includes models of individual teeth 120 and a model of the patient's gums 140. Various techniques for creating models of gum tissue and individual teeth from the IDDS are described in, for example, U.S. patent application Ser. Nos. 09/264,547 and 09/311,941.

Furthermore, FIG. 2A shows a portion of another gingival model 200 (a "secondary" gingival model), which is constructed to overlie gingival model 140 derived from the IDDS (the "primary" gingival model). The program uses the secondary gingival model 200 to model the deformation of the gingival tissue around the patient's teeth as the teeth move from their initial positions to their final positions. This ensures that orthodontic appliances made from positive molds of the patient's dentition fit comfortably around the patient's gums at all treatment stages. The secondary gingival model 200 also adds thickness to the gum model, which ensures that the orthodontic appliances do not press too tightly against the patient's gums.

Reference will now be made to various exemplary embodiments of the invention, which are illustrated in the accompanying figures. While these exemplary embodiments are described in sufficient detail to enable those skilled in the art to practice the invention, it should be understood that other embodiments may be realized and that logical and/or mechanical changes may be made without departing from the spirit and scope of the invention. Thus, the various embodiments herein are presented for purposes of illustration and not by way of limitation. For example, the steps recited in any of the method or process descriptions may be executed in any order and are not limited to the order presented. Moreover, any of the functions or steps may be outsourced to or performed by one or more third parties.

For the sake of brevity, conventional data networking, application development, and other functional aspects of the systems (and components of the individual operating components of the systems) may not be described in detail herein. Furthermore, the connecting lines shown in the various figures contained herein are intended to represent exemplary functional relationships and/or physical connections between the various elements. It should be noted that many alternative and/or additional functional relationships or physical connections may be present in a practical system.

Various embodiments of the present invention include one or more computing devices having programs stored therein for staging the movement of a patient's teeth. The computing device(s) or various components of any computing device discussed herein may include one or more of the following: a host server or other computing systems including a processor for processing digital data; a memory coupled to the processor for storing digital data; an input digitizer coupled to the processor for inputting digital data; an application program stored in the memory and accessible by the processor for directing processing of digital data by the processor; a display device coupled to the processor and memory for displaying information derived from digital data processed by the processor; and a plurality of databases. Various file indexes and/or databases used herein may include: client data; merchant data; and/or other similar useful data.

As those skilled in the art will appreciate, any computing device utilized by a user may include an operating system (e.g., Windows NT, 95/98/2000, OS2, UNIX, Linux, Solaris, MacOS, etc.) as well as various conventional support software and drivers typically associated with computers. As will be appreciated by one of ordinary skill in the art, each computing device may be embodied as a customization of an existing system, an add-on product, upgraded software, a stand alone system, a distributed system, a method, a data processing system, a device for data processing, and/or a computer program product. Accordingly, any program stored therein may take the form of an entirely software embodiment, an entirely hardware embodiment, or an embodiment combining aspects of both software and hardware. Furthermore, any program may take the form of a computer program product on a computer-readable storage medium having computer-readable program code means embodied in the storage medium. Any suitable computer-readable storage medium may be utilized, including hard disks, CD-ROM, optical storage devices, magnetic storage devices, and/or the like.

In accordance with one exemplary embodiment, a computing device is configured to receive an electronic representation of the patient's teeth in an initial position taken by, for example, an intra-oral scanner (i.e., a CT scanner) based on an impression or partial impression of the patient's teeth. In addition, the computing device is configured to receive or generate an electronic representation of a desired final position for each of the patient's teeth. The program stored within the computing device is configured to analyze the initial and final positions, and automatically create a route for each tooth to move from its initial position to its final position. A set of aligners to move the teeth along the route in various stages is manufactured. In doing such, the program is configured to coordinate the movement of the teeth such that the simplest method of moving teeth is utilized based upon several factors (e.g., complexity of movement required, obstructions from other teeth, and the like).

Figure 2B:
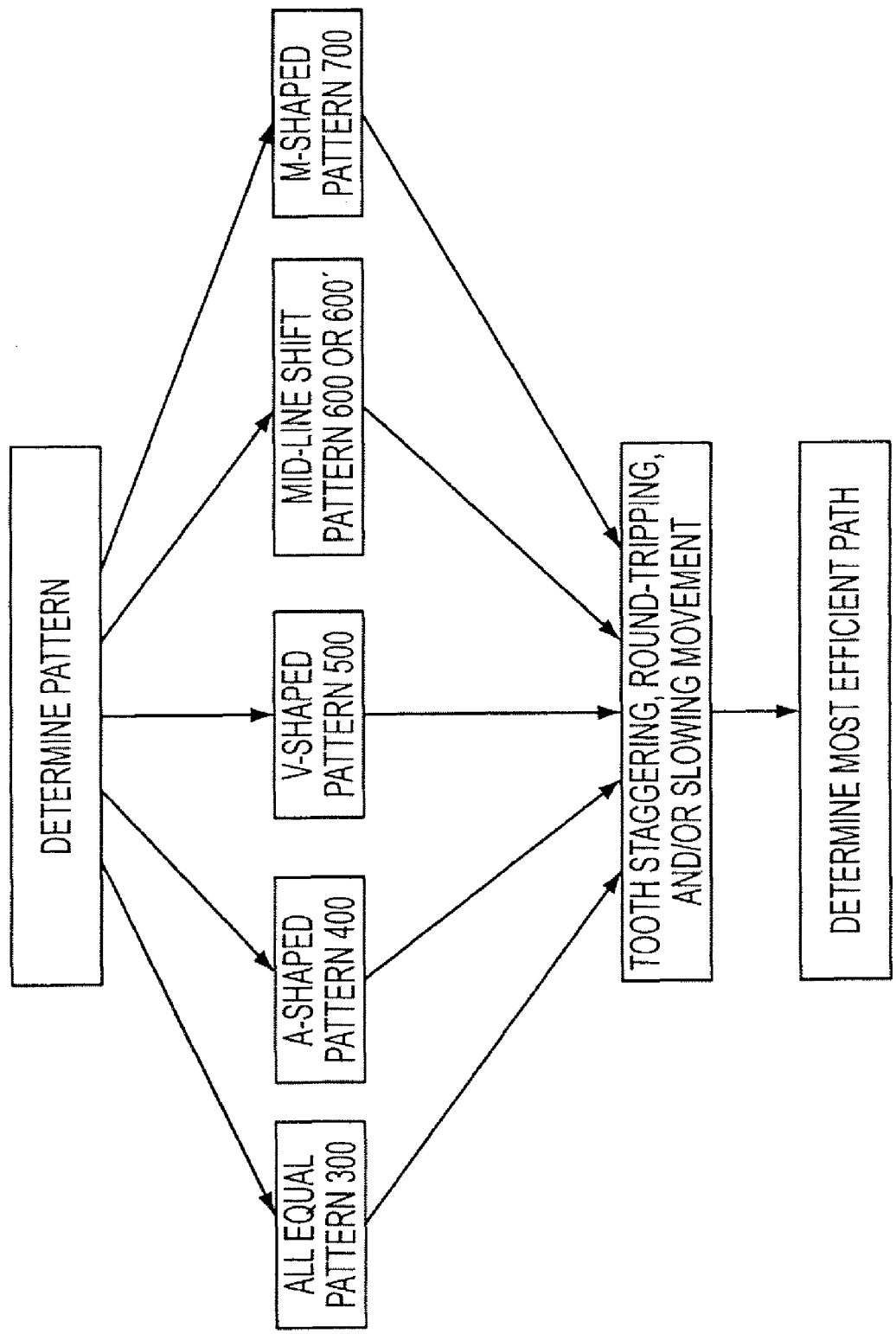
FIG. 2B is a flow diagram illustrating a plurality of patterns and options available to a computing device for optimizing the movement of a patient's teeth during treatment.

FIG. 2B is a flow diagram illustrating a plurality of patterns and options available to a system user and a computing device for optimizing the movement of a patient's teeth during treatment. After the computing device generates the electronic representation of the patient's teeth with respect to the desired final position, in accordance with an exemplary embodiment, the system user can decide which pattern, or combination of patterns thereof, to suitably utilize for moving the patient's teeth to achieve the desired final position, for example, by determining whether the patient's teeth does not require complex movements, and/or has gaps, crowding or are otherwise skewed. The computer program then calculates the planned stages in between the current and desired final position. If the patient does not require complex movements, an "all-equal" pattern 300 (discussed below) of teeth movement can be selected by the system user and utilized by the program. For patients having too much space between teeth (i.e., gaps between teeth), the system user can enable the program to be configured to utilize an "A-shaped" pattern 400 (discussed below) to coordinate the movement of the patient's teeth. For the opposite case (i.e., crowded teeth), the system user can enable the program to be configured to utilize a "V-shaped" pattern 500 (discussed below) to coordinate the movement of the patient's teeth. If a patient's teeth are skewed to the left or right of the patient's mid-line, a "Mid-Line Shift" pattern 600 (discussed below) for small shifts or a Mid-Line Shift pattern 600' (discussed below) can be selected by the system user to enable the program to coordinate the staged movement of the patient's teeth. For a set of teeth having gaps between both posterior and anterior teeth, the system user can enable the program to be configured to utilize an "M-shaped" pattern 700 (discussed below) to coordinate teeth movement. In addition, any other treatment patterns can be suitably selected from other orthodontic treatment patterns for treating space closure, reproximation, dental expansion, flaring, distalization, and/or lower incisor extraction, such as those patterns disclosed in U.S. Pat. No. 6,729,876, entitled "Tooth Path Treatment Plan" issued on May 4, 2004 and assigned to Align Technology, Inc.

Selection of a pattern, e.g., patterns for addressing all equal, gapped, crowded or skewed teeth, can be suitably determined by the system user through use of one or more command or input screens of a computing device. For example, in accordance with an exemplary embodiment, a computing device can be configured to allow the system user to assess the initial and desired final positions of a patient's teeth and then suitably select from such command screens appropriate movement patterns, as well as the extent or degree of stages within any pattern and/or the severity of the teeth misalignment, the speed of movement during treatment for each of the teeth and other treatment criteria. Such a configuration can include various known orthodontic treatment protocols, or any devised hereinafter.

While an exemplary embodiment may be configured to have a system user select a suitably pattern for treatment, in accordance with another exemplary embodiment, the computer program can be suitably configured to determine and select such a pattern. For example, by measuring distances of movement needed and/or otherwise analyzing the electronic representation of the patient's teeth in initial and final positions, and then based on algorithms to determine whether the teeth need approximately all-equal movement, or whether the teeth are gapped, crowded or skewed, or some combination thereof, the computer program can select a suitable pattern for treatment planning.

After the system user and/or computer program has decided which pattern to utilize, the system user can determine, and/or computer program is configured to determine, if the pattern should be modified to accommodate the teeth movement of the current patient to avoid collision. In accordance with an exemplary embodiment, to determine whether a collision is likely, the computer program can suitably calculate distances between a first tooth and a second tooth and then apply geometrical techniques, such as those disclosed in disclosed in U.S. Pat. No. 6,729,876, entitled "Tooth Path Treatment Plan" issued on May 4, 2004 and assigned to Align Technology, Inc.

In one embodiment, the program is configured to "stagger", "round trip" and/or slow the movement (each of which is discussed below, respectively) of one or more teeth if the patient's teeth cannot be moved without colliding with and/or obstructing another tooth/teeth. Based on that assessment, the program determines the most efficient path to take through some combination of patterns and accommodation of movement thereof.

As discussed above, for patients that do not require complex tooth movement coordination between multiple teeth or for teeth needing relatively simple correction, the program is configured to utilize an "all-equal" pattern in staging a set of aligners to correct the teeth. In accordance with one exemplary embodiment of the invention, the "all-equal" pattern provides that all of a patient's teeth move in parallel with one another. In other words, all of the patient's teeth that need to move begin moving at the same stage, and finish moving at the same stage.

Since each tooth begins and ends at the same stage, and the distance each tooth needs to travel may differ, the rate at which each tooth will move will generally vary. Specifically, the rate at which any one tooth will move generally depends upon how many total stages are needed to treat the patient, wherein the total number of stages needed for the treatment is the number of stages needed to place all of the teeth in their respective final positions. As such, the total number of stages needed for treatment is the number of stages needed for the tooth requiring the greatest number of stages for it to reach its final position. For example, if a first tooth needs five stages (at its maximum rate) of to reach its final position, a second tooth needs nine stages (at its maximum rate) to reach its final position, and a third tooth needs seven stages (at its maximum rate) to reach its final position, the total number of stages needed for treatment is nine stages. Moreover, the rate of the first and third teeth will generally be reduced, respectively, to accommodate the increased number of stages. As such, the first tooth will move at a rate of approximately five-ninths (5/9) its maximum rate, and the third tooth will move at a rate of seven-ninths (7/9) its maximum rate. Thus, each of these teeth will reach their final position at the same stage (i.e., stage 9).

The system user and/or program can suitably select a rate of tooth movement for each stage, such as by system user input on a command screen, or by computer algorithm. In accordance with one exemplary embodiment, the maximum rate at which a tooth can move is approximately 0.25 millimeters per stage (mm/stage), based in part upon physical limitations of movement of the certain teeth, such as the incisors. However, this maximum rate is capable of being higher or lower depending upon the patient's comfort level and/or tolerance for pain. In other words, the maximum rate at which the teeth move should be such that it does not cause significant discomfort or pain to the patient, but allows fast, efficient movement. The minimum rate can be any rate greater than zero, with the understanding that slower rates mean more stages and longer treatment times.

Figure 3:
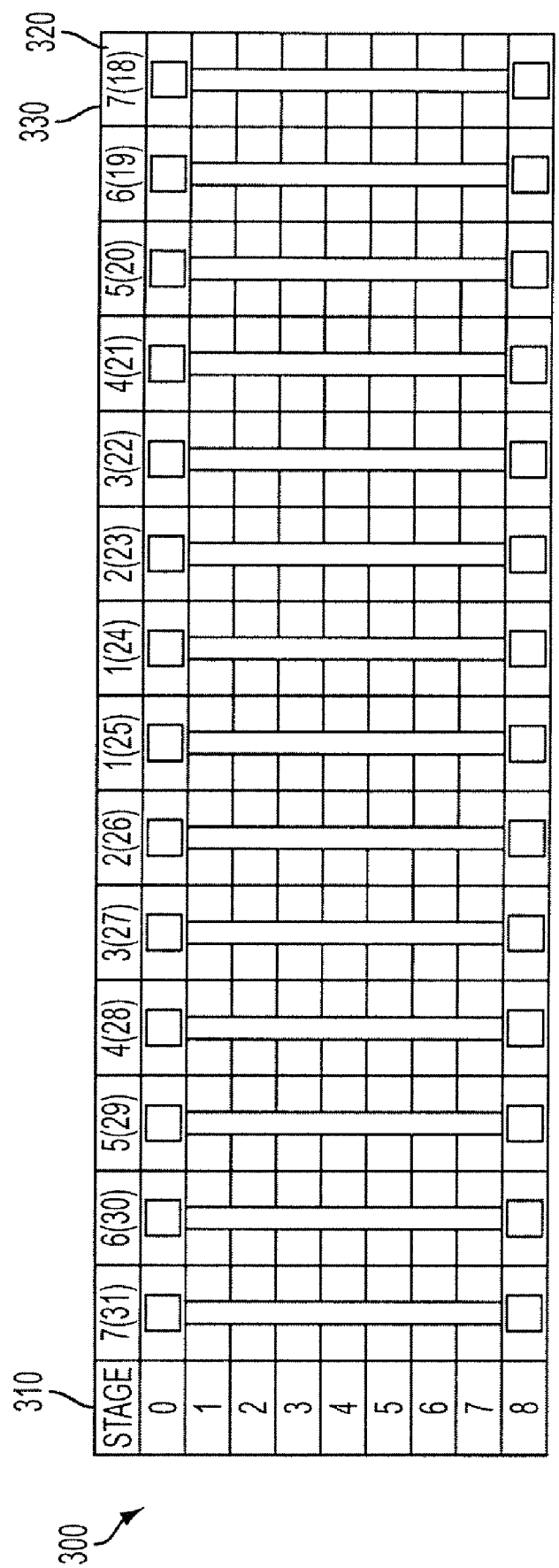
FIG. 3 is a diagram of an exemplary embodiment of an "all-equal" pattern for moving the teeth of a patient during an orthodontic treatment.

FIG. 3 is a diagram representing one example of an "all-equal" pattern 300 for moving the teeth of a patient in accordance with one exemplary embodiment of the invention. Column 310 depicts the number of stages for this particular treatment (i.e., stage 0 through stage 8), wherein stage 0 represents the patient's current teeth positioning, and stage 8 represents the final teeth positioning (or a final desired position for each respective tooth). The remaining columns depict the tooth number 320 according to the standard tooth numbering system, and the position number 330 (i.e., the relative position of each tooth on the patient's jaw arch). Notably, for illustration purposes it is assumed that the patient is not missing any teeth.

Recall, each tooth in an "all-equal" pattern is configured to be moved at the same time and for the same number of stages. Tooth movement is represented by the solid line connecting the teeth from their initial position (i.e., stage 0) to their final position (i.e., stage 8). Thus, FIG. 3 depicts each of teeth 18 through 31 moving at the same time through stages 1 through 7 until they reach their desired final position at stage 8.

For a set of teeth having gaps between at least two posterior teeth, the program is configured to utilize an "A-shaped" pattern in staging a set of aligners to correct the teeth. In accordance with one exemplary embodiment of the invention, the "A-shaped" pattern provides that teeth having the same and/or similar positions on the arch will be moved beginning at the same stage, and will move continuously until they reach their final position. Moreover, the "A-shaped" pattern begins by moving the most anterior-positioned teeth (e.g., the incisors, or teeth in positions 1 and/or 2) then sequentially moving the next posterior-positioned teeth until all of the teeth reach their final position. In accordance with an exemplary embodiment, the next posterior-positioned teeth are not scheduled to begin moving until at least approximately the half-way stage of its respective anterior-positioned teeth. For this and any of the other treatment patterns below, allowing movement of numerous teeth significantly earlier than half-way can result in undesirable pain, particularly in larger teeth, and attempting to move teeth too fast can cause the teeth to lose anchorage as well. On the other hand, allowing movement significantly later than approximately half-way delays treatment by increasing the total number of stages, and thus aligners needed. In accordance with an aspect of one exemplary embodiment, no more than two posterior teeth on one side of the arch may move simultaneously. In the event it is determined that the teeth may collide, such as the incisors if they move at the same time, then the movement of the incisors may be "staggered", "round-tripped", and/or include slower rates of movement (discussed below) to prevent them from colliding with and/or obstructing one another.

For example, a set of incisors may need six stages to move from their starting position to their final position. This means that the patient's pair of canines will not begin moving until at least approximately the incisors' stage 3. Furthermore, the patient's bicuspids are not scheduled to begin moving until the canines' stage 2 since the canines need 3 stages to move. This staging process continues until all of the patient's teeth reach their final position.

In accordance with one exemplary embodiment, the maximum rate at which the incisors may be configured to move is approximately 0.25 mm/stage, and the maximum rate at which the remaining teeth may be configured to move is approximately 0.33 mm/stage. However, similar to above, these maximum and/or selected rates are capable of being higher and/or lower depending upon the patient's comfort level and/or tolerance for pain.

Figure 4:
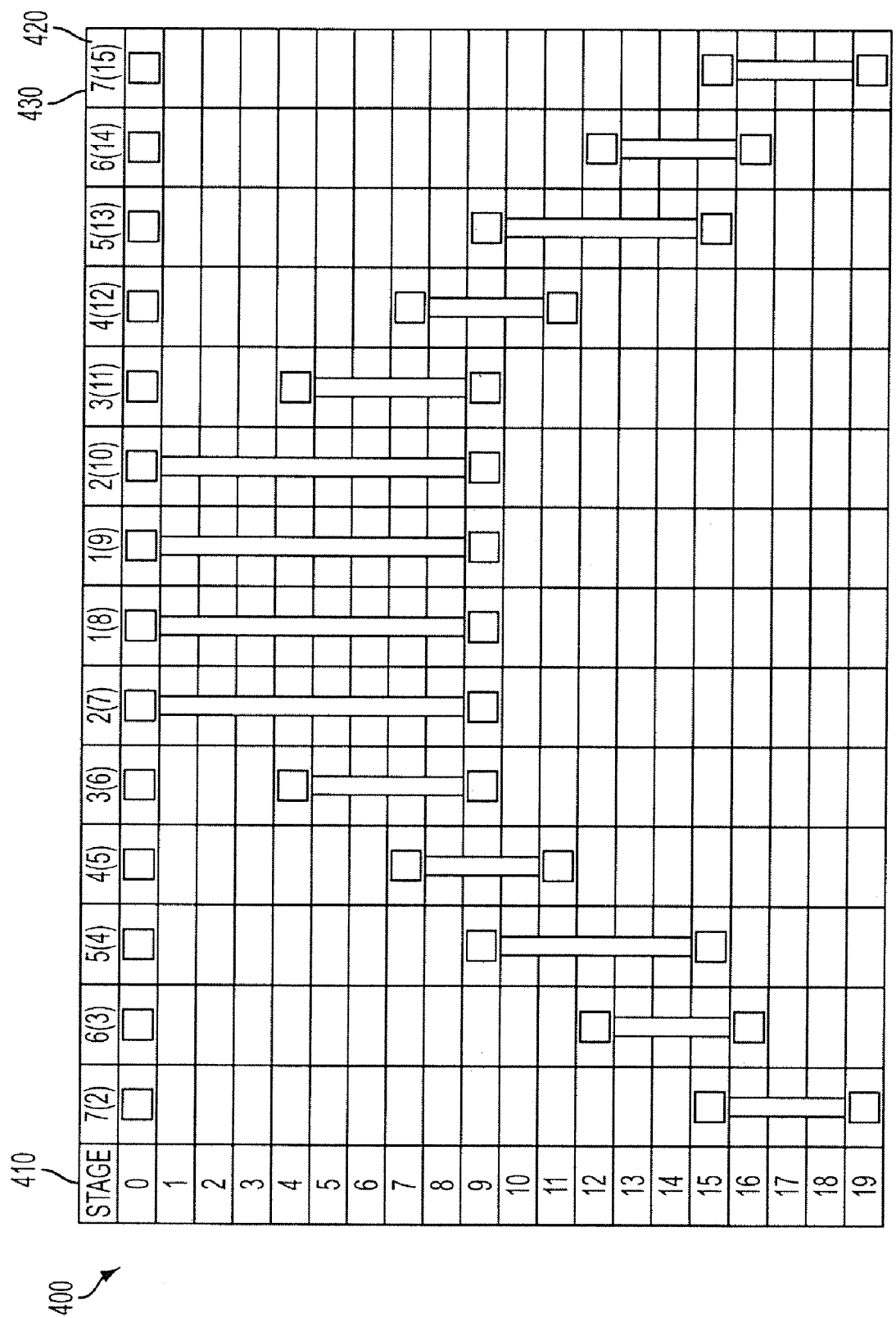
FIG. 4 is a diagram of one exemplary embodiment of an "A-shaped" pattern for moving the gapped teeth of a patient during an orthodontic treatment.

FIG. 4 is a diagram illustrating an example of an "A-shaped" pattern 400 in accordance with one exemplary embodiment of the invention. Similar to above, Column 410 illustrates the number of stages needed to correct the patient's teeth. In this example, the patient requires 18 stages of treatment before the patient's teeth reach their final position in stage 19. Moreover, similar to FIG. 3, FIG. 4 uses the standard teeth numbering system 420 to identify each of the teeth and a position 430 to illustrate the respective positioning of the teeth on the patient's arch.

Pattern 400 initiates by moving teeth 7, 8, 9, and 10 (i.e., the incisors) in stage 1. These teeth move in stages 1 through 8 to reach their final position in stage 9, but are not moved in stages 9 through 19. The solid lines represent the movement of teeth 7, 8, 9, and 10 in stages 1 through 8, and the lack of such solid lines in stages 9 through 19 represent the non-movement of teeth 7, 8, 9, and 10. Notably, the black boxes represent initial or final tooth positions, wherein no tooth movement occurs.

Next, the teeth in position 3 (i.e., teeth 6 and 11) are moved in stages 5 through 8, but are not moved in stages 1 through 4 or in stages 9 through 19. Teeth 6 and 11 are not scheduled to move until at least approximately the middle stage (i.e., stage 4) of the previous tooth movement. In other words, teeth 7 through 11 move a total of 8 stages and teeth 6 and 11 are not scheduled to move prior to stage 4 of those 8 stages.

After the teeth in position 3 have moved at least half way (i.e., 2 stages), the teeth in position 4 (i.e., teeth 5 and 12) are scheduled to begin moving. Teeth 5 and 12 are scheduled to begin moving no sooner than in stage 7 and continue moving until their final position in stage 11. In one embodiment, teeth 5 and 12 do not move in stages 1 through 7, or in stages 11 through 19.

The teeth in position 5 (i.e., teeth 4 and 13) are the next teeth scheduled to move in pattern 400, but no sooner than the middle stage (i.e., stage 9) for the teeth in position 4. Teeth 4 and 13 are scheduled to begin moving in stage 10 and continue to move until reaching their final position in stage 15. In one embodiment, teeth 4 and 13 do not move in stages 1 through 9, or in stages 15 through 19.

Next, the teeth in position 6 (i.e., teeth 3 and 14) are schedule to move, but no sooner than the half way point (i.e.

stage 12 or later) of the teeth in position 5. Teeth 3 and 14 are scheduled to begin moving in stage 13 and continue to move until reaching their final position in stage 16. Furthermore, similar to above, teeth 3 and 14 do not move in stages 1 through 12, or in stages 16 through 19.

Final teeth movement in pattern 400 is scheduled to begin no earlier than in stage 14 for teeth in position 7 (i.e., teeth 2 and 15). Teeth 2 and 15 are scheduled to begin movement in stage 16 and continue to move until reaching their final position in stage 19. Moreover, teeth 2 and 15 do not move in stages 1 through 15.

For a set of teeth lacking space in between at least two teeth (i.e., over-crowding), the program is configured to utilize a "V-shaped" pattern in staging a set of aligners to correct the teeth. In accordance with one exemplary embodiment of the invention, the "V-shaped" pattern provides that teeth having the same and/or similar positions on the arch will be moved beginning at the same stage, and will move continuously until they reach their final position. Moreover, the "V-shaped" pattern begins by moving the most posterior-positioned teeth (e.g., the molars, or teeth in position 7 and/or 8) then sequentially moving the next anterior-positioned teeth until all of the teeth reach their final position. The next anterior-positioned teeth are not scheduled to begin moving until at least approximately the half-way stage of its respective posterior-positioned tooth. In accordance with an aspect of one exemplary embodiment, no more than two posterior teeth on one side of the arch may move simultaneously, but all of the incisors move simultaneously during the final stages of the treatment. In one embodiment, if the teeth, e.g., incisors, will collide if they move at the same time, then the teeth may be "staggered", "round-tripped", and/or slowed (discussed below) to prevent them from colliding with one another.

In accordance with one exemplary embodiment, the maximum rate at which the incisors move may be configured to be approximately 0.25 mm/stage, and the maximum rate at which the remaining teeth move may be configured to be approximately 0.33 mm/stage. However, similar to above, these maximum and/or selected rates are capable of being higher or lower depending upon the patient's comfort level and/or tolerance for pain.

Figure 5:
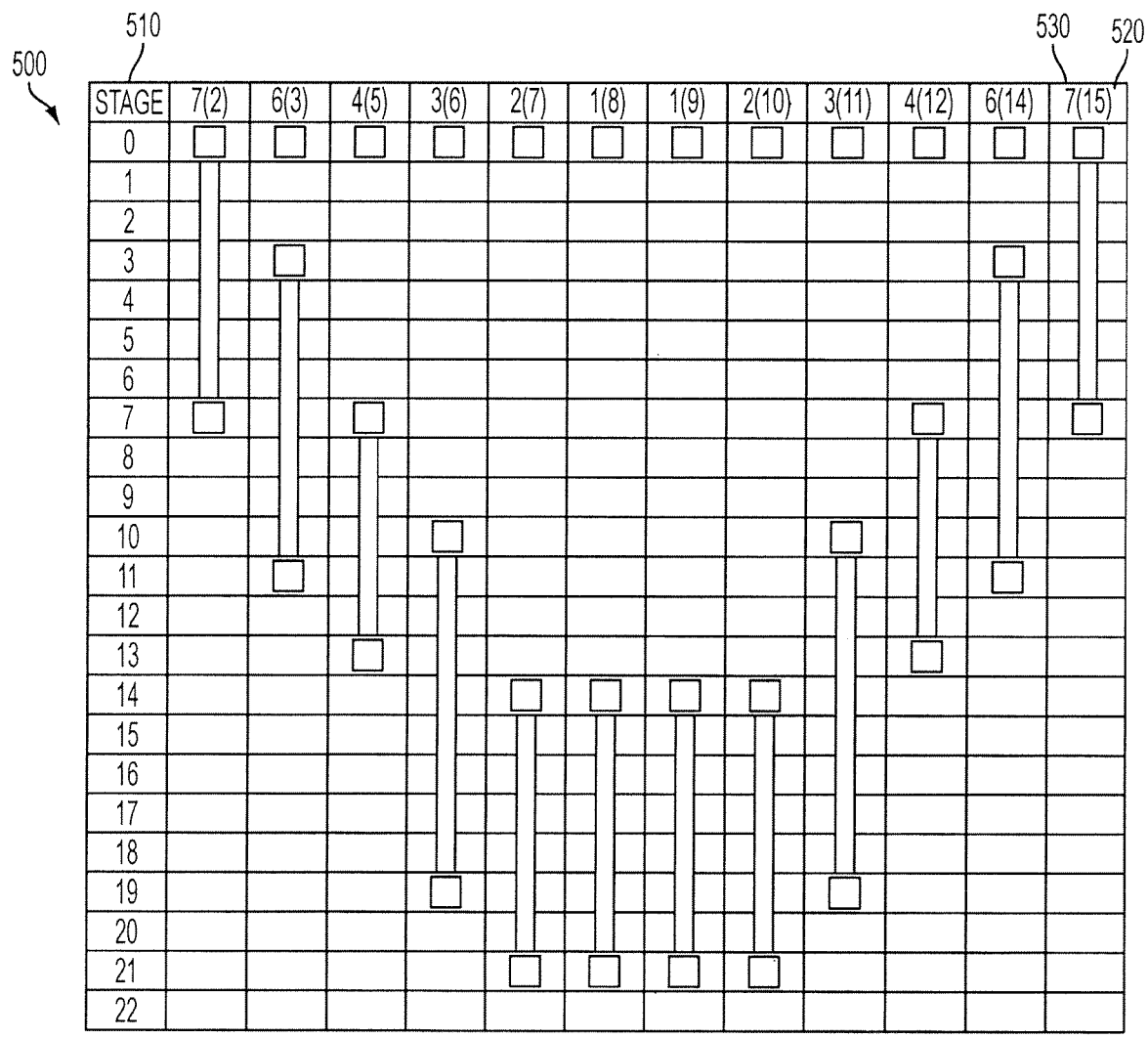
FIG. 5 is a diagram of an exemplary embodiment of a "V-shaped" pattern for moving the crowded teeth of a patient during an orthodontic treatment.

FIG. 5 is a diagram illustrating an example of a "V-shaped" pattern 500 in accordance with one exemplary embodiment of the invention. Similar to above, column 510 illustrates the number of stages needed to correct the patient's teeth. In this example, the patient requires 20 stages of treatment before the patient's teeth reach their final position in stage 21. Moreover, similar to FIGS. 3 and 4, FIG. 5 uses the standard teeth numbering system 520 to identify each of the teeth and a position 530 to illustrate the respective positioning of the teeth on the patient's arch.

Pattern 500 initiates by moving teeth in position 7 (i.e., the molars numbered as teeth 2 and 15) in stage 1. These teeth continue to move in stages 1 through 6 to reach their final position in stage 7, but are not moved in stages 8 through 21. Next, the teeth in position 6 (i.e., teeth 3 and 14) are moved in stages 4 through 10, but are not moved in stages 1 through 3 or in stages 10 through 21. In one embodiment, teeth 3 and 14 are not scheduled to move until at least approximately the middle stage (i.e., stage 3) of the previous tooth movement. In other words, teeth 2 through 15 move a total of 6 stages, and teeth 3 and 14 are not scheduled to begin moving their seven stages prior to stage 3 of teeth 2 and 15's 6 stages.

In this example, the patient does not need the teeth in position 5 (i.e., teeth 4 and 13) to move. Thus, after the teeth in position 6 have moved half way (i.e., 4 stages), the teeth in position 4 (i.e., teeth 5 and 12) are scheduled to begin moving.

Teeth 5 and 12 are scheduled to begin moving no sooner than in stage 7 and continue moving until their final position in stage 12. In one embodiment, teeth 5 and 12 do not move in stages 1 through 7, or in stages 13 through 21.

The teeth in position 3 (i.e., teeth 6 and 11) are the next teeth scheduled to move in pattern 500, but no sooner than the middle stage (i.e., stage 10) for the teeth in position 4. Teeth 6 and 11 begin moving in stage 11 and continue to move until reaching their final position in stage 19. In one embodiment, teeth 6 and 11 do not move in stages 1 through 10, or in stages 19 through 21.

Final teeth movement in pattern 500 is scheduled to begin no earlier than in stage 14 for teeth in positions 2 and 1 (i.e., the incisors numbered as teeth 7, 8, 9, and 10). Teeth 7 through 10 are scheduled to begin movement in stage 15 and continue to move until reaching their final position in stage 21. Similar to above, teeth 7 through 10 do not move in stages 1 through 14.

For a set of teeth that is off-centered (i.e., skewed to one side), the program is configured to utilize a "mid-line shift" pattern in staging a set of aligners to correct the teeth. In accordance with one exemplary embodiment of the invention, the mid-line shift pattern provides that tooth movement begins on one side of the patient's arch to center the teeth with respective to the mid-line of the patient's mouth. The next tooth/teeth to move is/are not scheduled to begin moving until at least approximately the half way stage of its respective previously-scheduled tooth/teeth. For example, if the patient's teeth are skewed to the left, tooth movement begins by moving the most-posterior tooth on the right side of the patient's arch to the right, and then progressively shifting the teeth towards the right filling in the space vacated by the previously-moved tooth. The opposite is true for teeth skewed to the right.

For situations where the patient's teeth need to shift less than about 1.0 mm, in one embodiment of the invention, the incisors move simultaneously during an intermediate stage of the treatment. In one embodiment, if the incisors will collide and/or obstruct one another if they move at the same time, then the incisors may be "staggered", "round-tripped", and/or slowed (discussed below) to prevent them from doing such. In another embodiment of the invention, when the patient's mid-line needs to shift greater than about 1.0 mm, each of the incisors is scheduled to move independent of the other incisors. In yet another exemplary embodiment of the invention, no more than two posterior teeth on one side of the arch may move simultaneously regardless of the amount of shift required.

In accordance with one exemplary embodiment of the invention, the maximum rate at which the incisors move may be configured to be approximately 0.25 mm/stage, and the maximum rate at which the remaining teeth move may be configured to be approximately 0.33 mm/stage. However, similar to above, these maximum and/or selected rates are capable of being higher or lower depending upon the patient's comfort level and/or tolerance for pain.

Figure 6A:
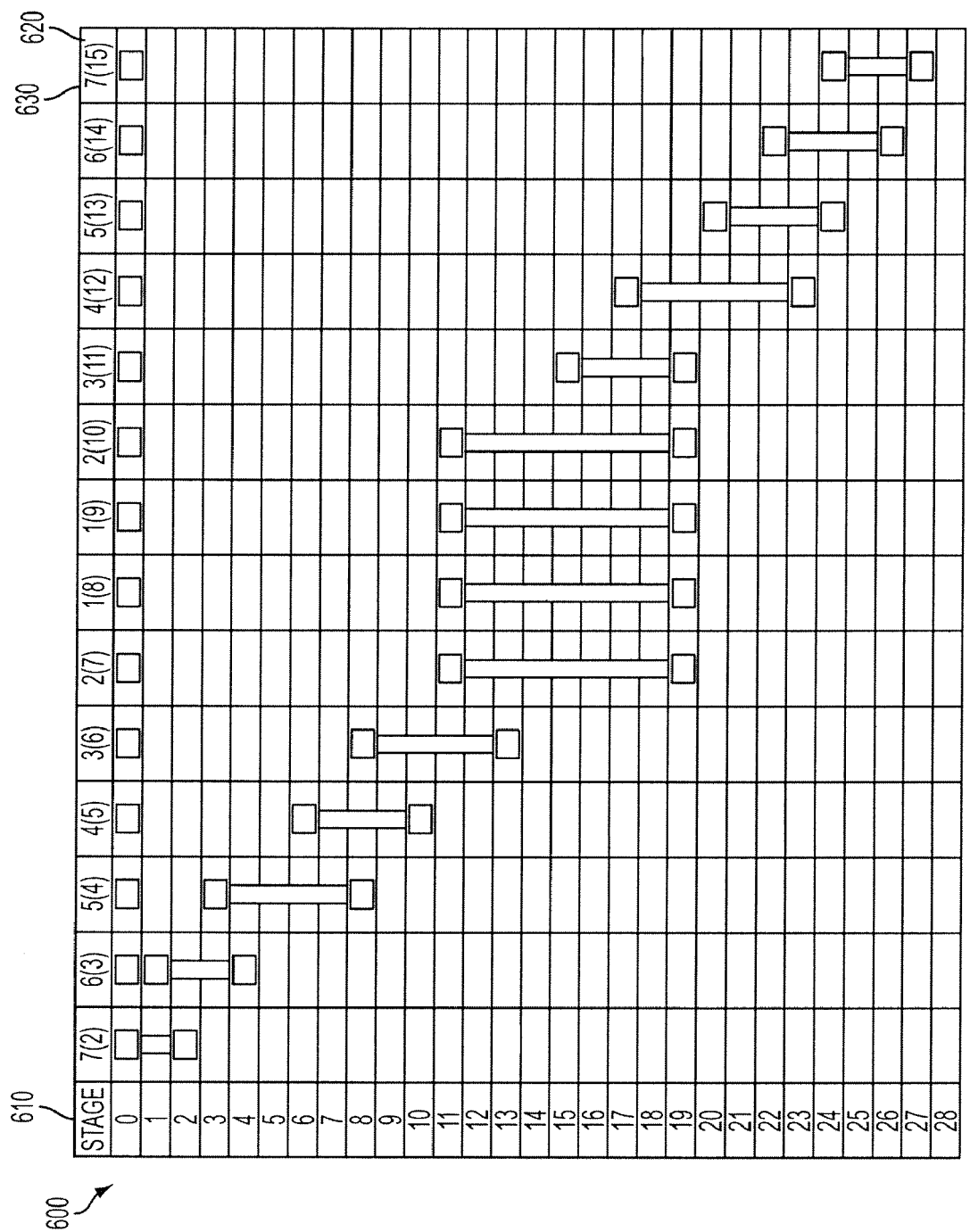
FIG. 6A is a diagram of one exemplary embodiment of a "Mid-Line Shift" pattern for moving the skewed teeth of a patient during an orthodontic treatment.

FIG. 6A is a diagram illustrating an example of a "mid-line shift" pattern 600 for teeth skewed (to the patient's left) less than about 1.0 mm in accordance with one exemplary embodiment of the invention. Similar to above, column 610 illustrates the number of stages needed to correct the patient's teeth. In this example, the patient requires 26 stages of treatment before the patient's teeth reach their final position in stage 27. Moreover, similar to FIGS. 3-5, FIG. 6A uses the standard teeth numbering system 620 to identify each of the teeth and a position 630 to illustrate the respective positioning of the teeth on the patient's arch.

Pattern 600 initiates by moving tooth 2 to the right in stage 1. Next, tooth 3 is moved to the right for 2 stages, followed by tooth 4 moving to the right for 2 stages. Tooth 5 moves next for 3 stages, followed by tooth 6 for 4 stages. The incisors (i.e., teeth 7 through 10) are scheduled to move next beginning in stage 11 (although they could have been scheduled as early as stage 10). As noted above, since the patient needs a mid-line shift less than about 1.0 mm, the incisors move together. The remaining teeth continue shifting sequentially to the right until all the teeth arrive in their respective final position in stage 27.

In one embodiment, the teeth are not scheduled to move after they have reached their respective final positions. Furthermore, the next tooth/teeth scheduled to move are not scheduled to move prior to at least approximately the half-way stage of the previously-scheduled tooth/teeth.

Figure 6B:
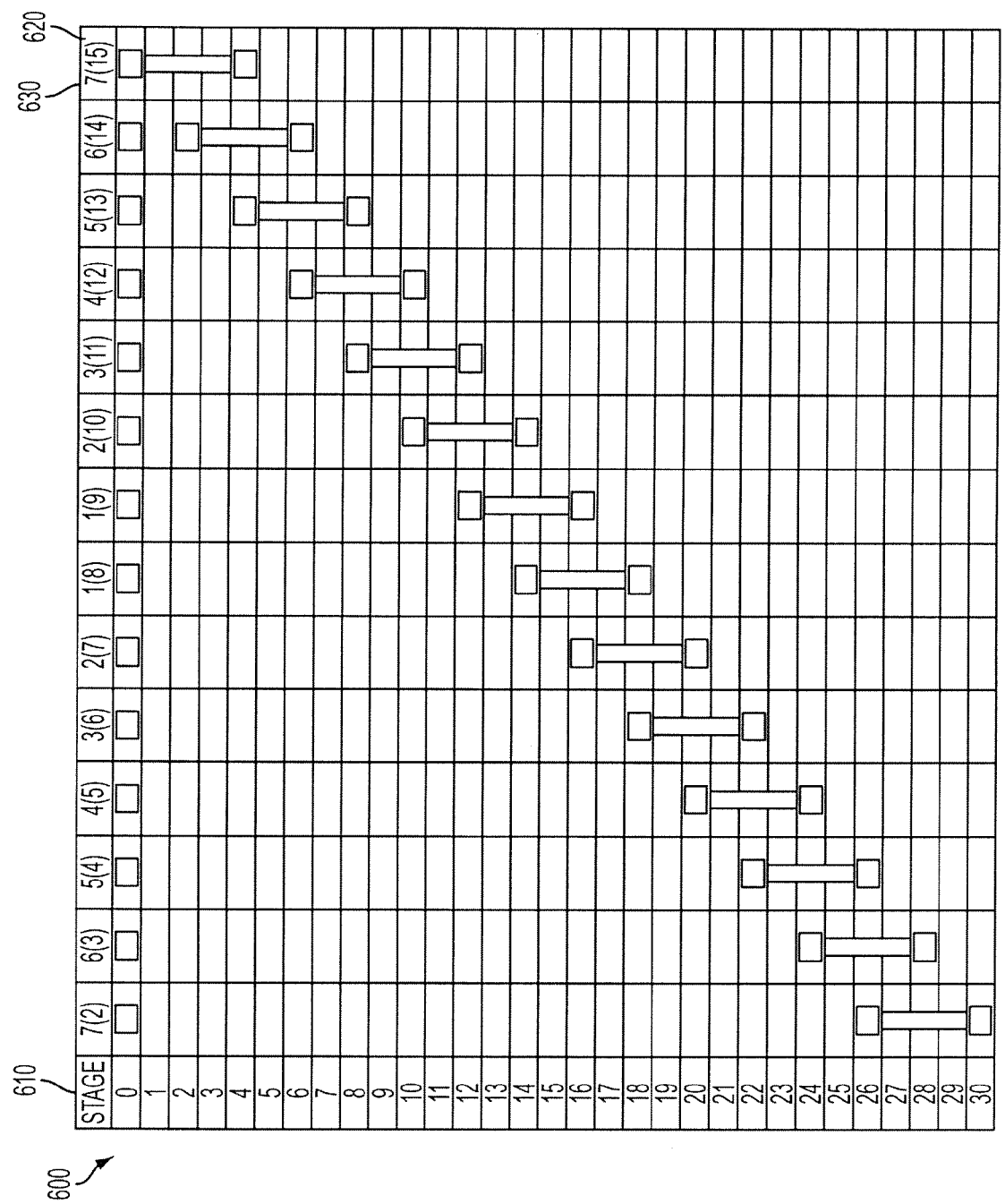
FIG. 6B is a diagram of an exemplary embodiment of another "Mid-Line Shift" pattern for moving the skewed teeth of a patient during an orthodontic treatment.

FIG. 6B is a diagram illustrating an example of an "mid-line shift" pattern 600' for teeth skewed (to the patient's right) more than about 1.0 mm in accordance with one exemplary embodiment of the invention. Similar to above, column 610 illustrates the number of stages needed to correct the patient's teeth. In this example, the patient requires 29 stages of treatment before the patient's teeth reach their final position in stage 30. Moreover, similar to FIG. 6A, FIG. 6B uses the stand teeth numbering system 620 to identify each of the teeth and a position 630 to illustrate the respective positioning of the teeth on the patient's arch.

Pattern 600 initiates by moving tooth 15 to the left 3 stages beginning in stage 1. Next, tooth 14 is moved to the left for 3 stages, followed by tooth 13 moving to the left for 3 stages. The remaining teeth continue shifting sequentially to the left until all the teeth arrive in their respective final position in stage 30. As noted above, since the patient needs a mid-line shift greater than about 1.0 mm, the incisors do not move together, but instead move individually. In one embodiment, the teeth are not scheduled to move after they have reached their respective final positions. Furthermore, the next tooth scheduled to move is not scheduled to move prior to at least approximately the half way stage of the previously-scheduled tooth.

For a set of teeth having gaps between posterior teeth and anterior teeth, the program is configured to utilize an "M-shaped" pattern in creating a set of aligners to correct the teeth. In accordance with one exemplary embodiment of the invention, the "M-shaped" pattern provides that teeth having the same and/or similar positions on the arch will be moved beginning at the same stage, and will move continuously until they reach their final position. Moreover, the "M-shaped" pattern begins by moving teeth between the anterior teeth and the posterior teeth (e.g., the bicuspids, or teeth in positions 4 and/or 5) then sequentially moving both the adjacent anterior and/or adjacent posterior teeth until all of the teeth reach their final position. Furthermore, the teeth, e.g., incisors, move simultaneously unless they will collide with or obstruct one another, wherein the incisors may be "staggered", "round-tripped", and/or slowed (discussed below) to prevent them from colliding with one another. In addition, similar to embodiments discussed above, subsequently scheduled teeth are not scheduled to begin moving until at least approximately the half-way stage of its respective precedent tooth. Moreover, the corresponding positions on each side of the patient's arch move during the same stage. In accordance with an aspect of one exemplary embodiment, no more than two posterior teeth on one side of the arch may move simultaneously.

In accordance with one exemplary embodiment, the maximum rate at which the incisors move may be configured to be approximately 0.25 mm/stage, and the maximum rate at which the remaining teeth move may be configured to be approximately 0.33 mm/stage. However, similar to above, these maximum and/or selected rates are capable of being higher or lower depending upon the patient's comfort level and/or tolerance for pain.

Figure 7:
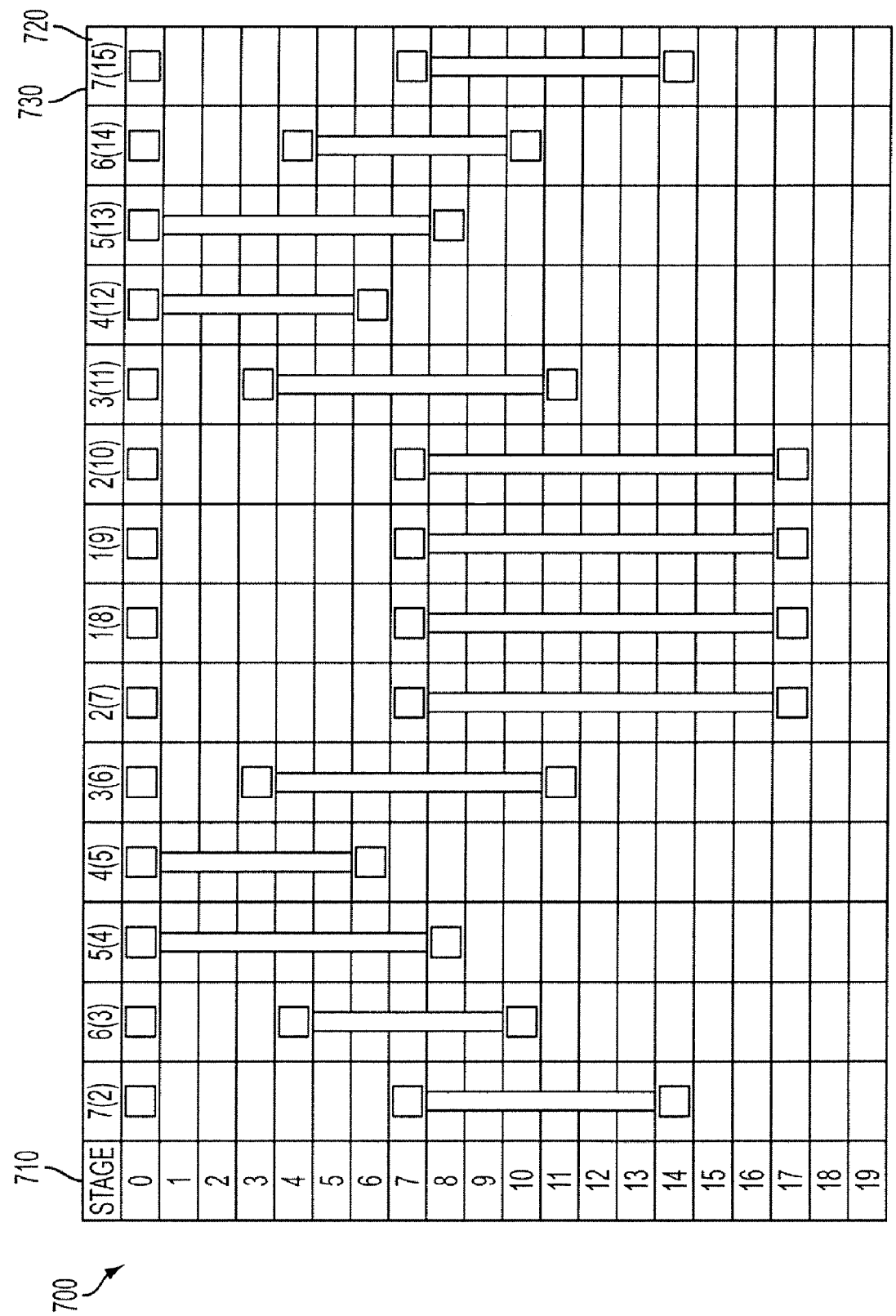
FIG. 7 is a diagram of one exemplary embodiment of an "M-shaped" pattern for moving the gapped teeth of a patient during an orthodontic treatment.

FIG. 7 is a diagram illustrating an example of an "M-shaped" pattern 700 in accordance with one exemplary embodiment of the invention. Similar to above, column 710 illustrates the number of stages needed to correct the patient's teeth, wherein, in this example, the patient requires 16 stages of treatment before the patient's teeth reach their final position in stage 17. Moreover, similar to FIGS. 3-6B, FIG. 7 uses the standard teeth numbering system 720 to identify each of the teeth and a position 730 to illustrate the respective positioning of the teeth on the patient's arch.

Pattern 700 initiates by moving teeth in positions 5 and 6 (i.e., the bicuspids) in stage 1. These teeth continue to move until they reach their final position, which, for example includes teeth 5 and 12 moving in stages 1 through 6, and teeth 4 and 13 moving in stages 1 through 8. Notably, these teeth need different numbers of stages to reach their final positions. As such, their respective adjacent teeth are scheduled to begin moving during different stages.

In the example illustrated in FIG. 7, teeth 5 and 12 need five stages of treatment, thus, teeth 6 and 11 are scheduled to begin moving at the mid-point (i.e., stage 3) of teeth 5 and 12's treatment. Similarly, teeth 4 and 13 need seven stages, thus, teeth 3 and 14 are not scheduled to begin movement until stage 4 of teeth 4 and 13's treatment. Subsequently, the next adjacent teeth are scheduled to move proximate the mid-point of stages of its respective adjacent tooth.

In accordance with one exemplary embodiment, the maximum rate at which the incisors move may be configured to be approximately 0.25 mm/stage, and the maximum rate at which the remaining teeth move may be configured to be approximately 0.33 mm/stage. However, similar to above, these maximum and/or selected rates are capable of being higher or lower depending upon the patient's comfort level and/or tolerance for pain.

As referenced above, in cases where teeth may collide with or obstruct one another during movement, the program is configured to suitably stagger, slow down and/or plan-round-tripping for the teeth movement. "Staggering" is the process of delaying one or more teeth from moving one or more stages where it would otherwise move in order to prevent another tooth from colliding with and/or obstructing the path of the delayed tooth. "Slowing down" is the process of having one or more teeth scheduled to move at a rate less than the rate of other teeth, or even stopping using interim key frames, so that collisions and/or obstructions do not occur. "Round-tripping" is the technique of moving a first tooth out of the path of a second tooth, and once the second tooth has moved sufficiently, moving the first tooth back to its previous position before proceeding to a desired final position of that first tooth. Such staggering, slowing down and/or round-tripping can be suitably applied alone or in combination, and in any order. In an exemplary embodiment, the computer program first attempts staggering of the teeth movement, followed by slowing-down/interim key frames if the staggering does not avoid collisions, and then followed by round-tripping as a last resort. In addition, each of staggering, slowing down and round-tripping techniques can be applied to any of the patterns discussed above, or any other movement patterns hereinafter developed in the field of orthodontics.

Figure 8:
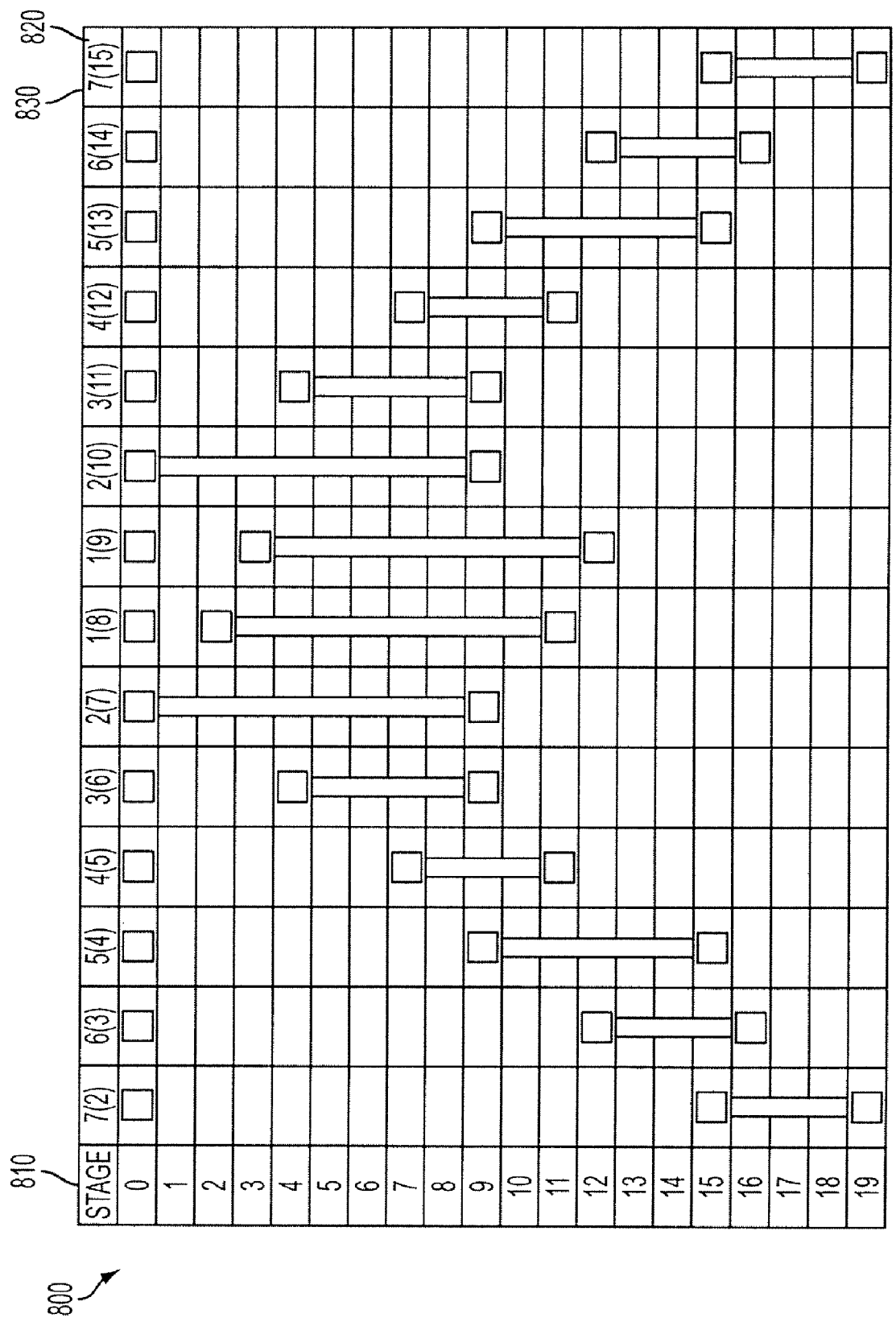
FIG. 8 is a diagram of the exemplary embodiment of FIG. 4 utilizing a staggering technique to avoid collisions with and/or obstructions between teeth during the orthodontic treatment.

FIG. 8 illustrates an example of the incisors of an "A-shaped" pattern 800 similar to the example of FIG. 4 with the teeth in position 1 (i.e., teeth 8 and 9) being staggered such that they do not collide with the teeth in position 2 (i.e., teeth 7 and 10). In this example, teeth 7 and 10 are scheduled to begin movement in stage 1. In a typical "A-shaped" pattern, teeth 8 and 9 would also begin movement in stage 1. However, if this were performed for the patient of this example, tooth 8 would collide with tooth 7 and/or tooth 9. Likewise, tooth 9 would collide with tooth 8 and/or tooth 10. Thus, tooth 8 is not scheduled to begin moving until a later stage, e.g., stage 2, to prevent such a collision. Furthermore, tooth 9 is likewise not scheduled to begin movement until a later stage, e.g., stage 3, to prevent a collision with tooth 8 and/or tooth 10. By staggering the tooth movement, any tooth/teeth that may collide with another tooth is moved out of the path of other teeth to prevent any undesired collisions.

Notably, although the above example of staggering refers to the incisors, staggering techniques may be used to delay the movement of any tooth and/or teeth in order to prevent one or more teeth from colliding. Moreover, the remaining schedule for the other teeth in pattern 800 would be similar to the discussion above with respect to FIG. 4. Furthermore, the above staggering example is with reference to an "A-shaped", pattern, however, the above discussion is equally applicable to an "all-equal" pattern, a "V-shaped" pattern, a "Mid-Line Shift" pattern, and an "M-shaped" pattern.

In addition to staggering tooth movement, the program also includes the ability to avoid teeth from colliding with and/or obstructing one another utilizing round-tripping techniques, wherein a tooth is positioned of the path of another tooth, and then repositioned or otherwise redirected until a desired final position. In accordance with an exemplary embodiment, the round-tripping process can also include the use of interim key frames that comprise "just-in-time" stops of movement of a selected tooth or teeth for one or more stages.

Figure 9:
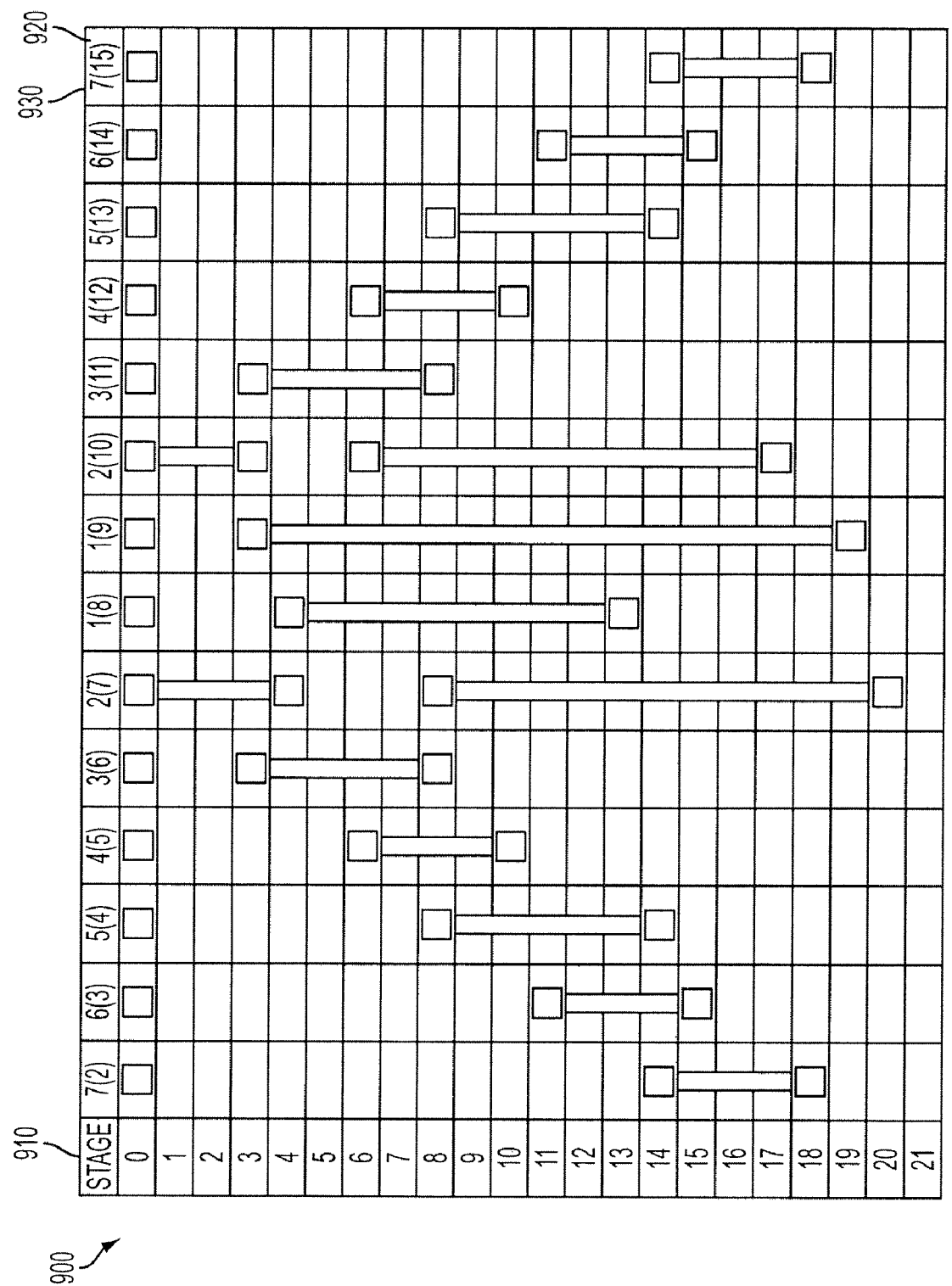
FIG. 9 is a diagram of the exemplary embodiment of FIG. 4 utilizing a round-tripping technique to avoid collisions with and/or obstructions between teeth during the orthodontic treatment.

FIG. 9 illustrates an example of the incisors of an "A-shaped" pattern 900 similar to the example of FIG. 4 with the teeth in position 2 (i.e., teeth 7 and 10) being moved out of the way of tooth 8 and tooth 9, respectively. Recall in FIG. 4, tooth 7 is scheduled to move 8 stages. In this example, tooth 7 is moved out of the way of tooth 8 for 3 stages (i.e., stages 1 through 3), tooth 8 takes 4 stages to pass through tooth 7's previous position (i.e., stages 4 through 7), tooth 7 is moved back 3 stages to return to its previous position (i.e., stages 8 through 10), and then tooth 7 is moved its originally scheduled 8 stages (i.e., stages 11 through 18) to reach its final position in stage 19.

Similarly, recall in FIG. 4 that tooth 9 is also scheduled to move 8 stages. In the example of FIG. 9, tooth 10 is moved out of the way of tooth 9 for 2 stages (i.e., stages 1 and 2), tooth 10 takes 4 stages to pass through tooth 10's previous position (i.e., stages 3 through 6), tooth 10 is moved back 2 stages to return to its previous position (i.e., stages 7 and 8), and then tooth 10 is moved its originally scheduled 8 stages (i.e., stages 9 through 16) to reach its final position in stage 17.

Notably, although the above example of round-tripping refers to the incisors, round-tripping techniques may be used to delay the movement of any tooth and/or teeth in order to prevent one or more teeth from colliding with and/or obstructing one another. Moreover, the remaining schedule for the other teeth in pattern 900 would be similar to the discussion above with respect to FIG. 4. Furthermore, the above round-tripping example is with reference to an "A-shaped" pattern, however, the above discussion is equally applicable to an all-equal pattern, a "V-shaped" pattern, a "Mid-Line Shift" pattern, and an "M-shaped" pattern.

Another technique utilized to avoid teeth from colliding with and/or obstructing one another is to slow the rate of movement of one or more teeth. As discussed above, the teeth ideally move at a maximum rate for each stage to reduce the overall number of stages of the treatment. When it is appropriate, one or more teeth can be scheduled to move at a rate less than the maximum rate, while other teeth can move at a constant and/or increased rate, so that collisions and/or obstructions do not occur. In addition to decreasing the rate of movement, the slow down process can also include the use of interim key frames that comprise "just-in-time" stops of movement of a selected tooth or teeth for one or more stages.

Figure 10A:
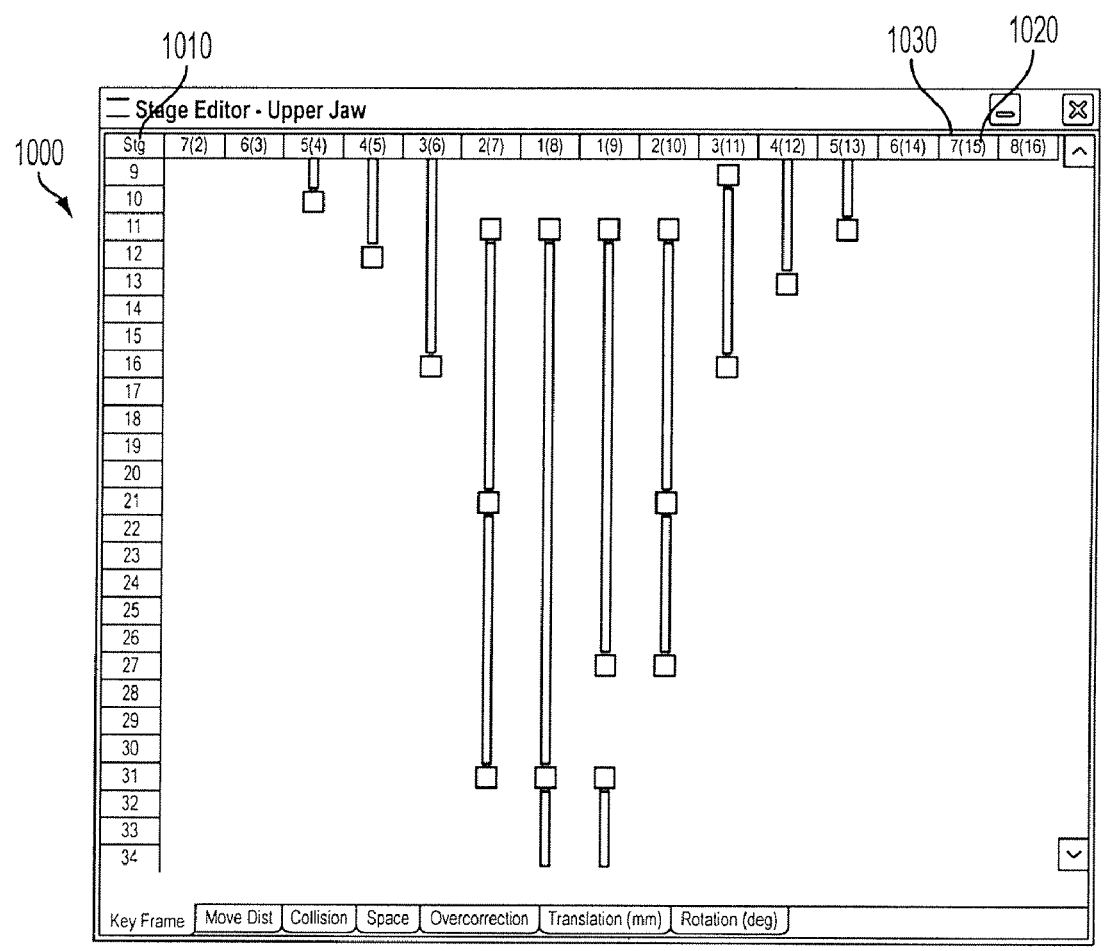
FIG. 10A is a diagram of the exemplary embodiment of FIG. 5 utilizing interim keyframes to avoid collisions with and/or obstructions between teeth during the orthodontic treatment.

For example, FIGS. 10A and 10B shows an example of varying rates of movement for the teeth, such as for the over-crowding of teeth using a V-shaped pattern as illustrated in FIG. 5. In this example, tooth 7 initially moves at a rate of 0.23 mm for each of stages 12 through 21, and then is slowed down to a rate of 0.16 mm for each of stages 22 through 27, then further slowed down to 0.15 mm for each of stages 28 through 31. Furthermore, the rate of movement for tooth 8 initially moves at a rate of 0.22 mm for 12 and 13, then sped up to a rate of 0.23 for each of stages 14 through 23, and then is further sped up to 0.24 mm for stages 24-31, before being slowed to 0.21 mm for each of stages 32 and 33. Thus, tooth 7 is slowed to a rate in which it will not collide and/or obstruct the movement of tooth 8 and/or other teeth during the tooth movement treatment.

Similarly, tooth 9 is scheduled to move at its maximum rate of 0.09 mm per stages for each of stages 12 and 13, then slightly sped up to 0.10 mm per stage for each of stages 14 through 27. Next, an interim key frame is applied through stages 28-31 of tooth 9 to stop all movement of tooth 9, before being increased back to a speed of 0.12 mm per stages for each of stages 32 and 33. Thus, tooth 9 is slowed to a rate in which it will not collide and/or obstruct the movement of tooth 8 and/or other teeth during the tooth movement treatment.

In this example, certain of the teeth, e.g., teeth 3, 4, 5, 6, 8, 10 and 11 can be configured to move proximate their maximum rate per stage for each of their respective stages of movement, with very slight increases and/or decreases in speed along the way since these teeth will not collide or obstruct one another during tooth movement. One the other hand, the rates of movement of teeth 7, 10 and 8 (using an interim key frame) are slowed to avoid such collisions.

Figure 11:
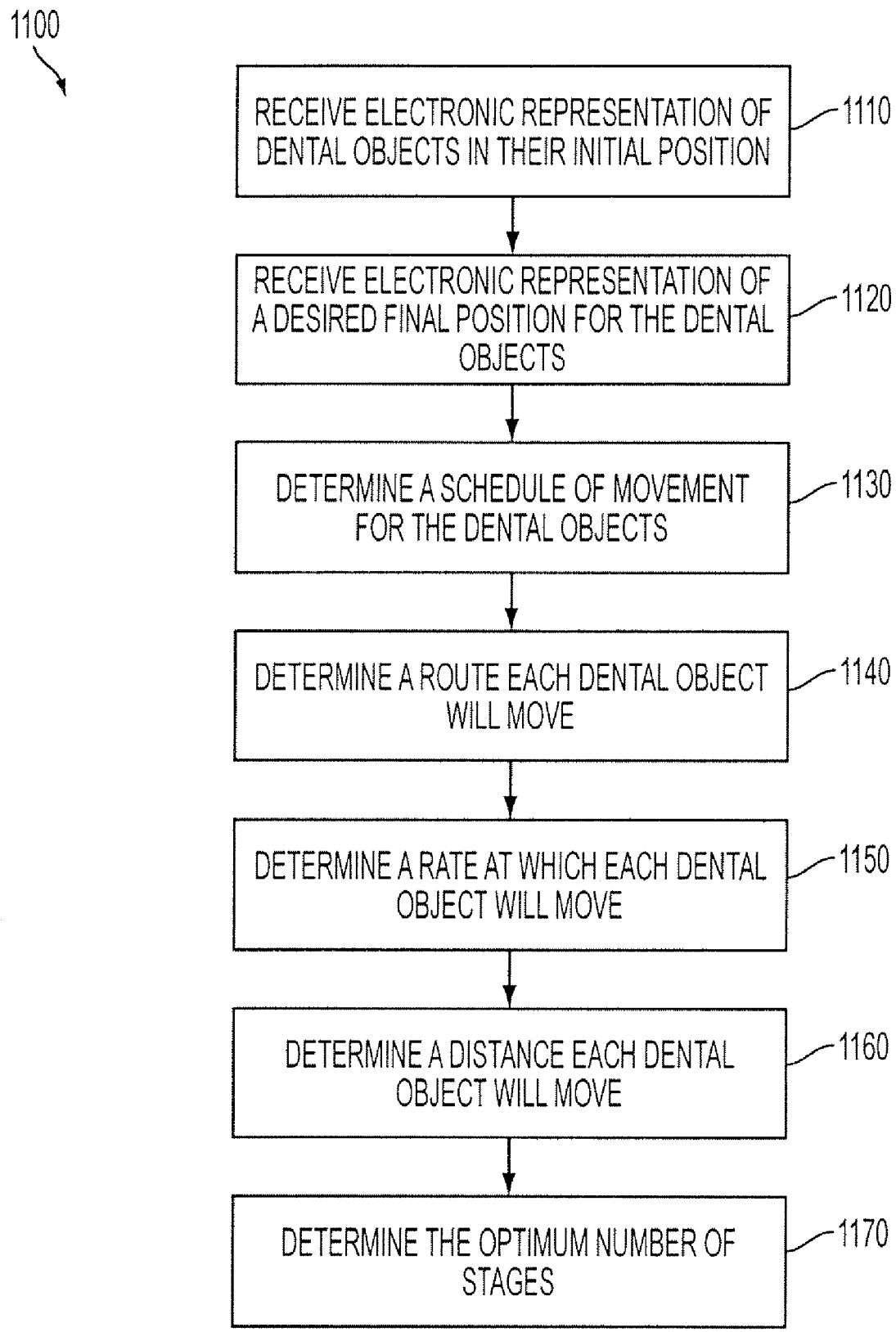
FIG. 11 is flow diagram of a method for scheduling the movement of teeth during an orthodontic treatment.

FIG. 11 is a flow diagram of one exemplary embodiment of a method 1100 to stage the movement of one or more teeth in accordance with one exemplary embodiment of the invention. Method 1100, in one embodiment, initiates by receiving an electronic representation of a patient's teeth in their initial positions (step 1110). Furthermore, method 1100 includes the step of receiving an electronic representation of the patient's teeth in a desired final position (step 1120).

In one exemplary embodiment of the invention, method 1100 includes the step of determining a schedule in which each tooth will move (step 1130). In accordance with an aspect of an exemplary embodiment, step 1130 includes the step of determining a route for each of the patient's teeth (step 1140). In another aspect of the invention, step 1130 includes the step of determining a rate each tooth will move (step 1150). Step 1130, in yet another aspect of the invention, includes the step of determining a distance each tooth will need to travel to reach its final position (step 1160).

Method 1100, in another exemplary embodiment of the invention, includes determining the optimum number of stages for a patient's treatment (step 1170). The optimum number of stages, in one embodiment, is determined based upon the determinations of step 1130 through step 1170. Furthermore, step 1170 includes factoring any staggering, slowing down/interim key framing, and/or round-tripping needed to place the patient's teeth in their desired final position. For example, in FIGS. 3-9 the optimum number of stages needed for these respective examples factored in the type of pattern needed, the rate, the path, the distance, staggering, slowing down/interim key framing, and/or round-tripping in determining the optimum number of stages for treating the patient's teeth. As one skilled in the art will recognize, the optimum number of stages will likely differ from patient to patient.

In one exemplary embodiment, determining the optimum number of stages includes determining the minimum number of stages needed for each respective tooth to be placed in its final, desired position. In another exemplary embodiment, the optimum number of stages is the largest number of the minimum stages needed to place the patient's teeth in their final, desired position. For example, a patient has three teeth that need to be moved during treatment, wherein the first tooth needs 4 stages to move to its final position, the second tooth needs 9 stages to move to its final position, and the third tooth needs 6 stages to move to its final position. Assuming each of these teeth is scheduled to begin moving at the same stage, the optimum number of stages is 9 since this is the minimum number of stages needed to place all of the teeth in their final position.

Benefits, other advantages, and solutions to problems have been described herein with regard to specific embodiments. However, the benefits, advantages, solutions to problems, and any element(s) that may cause any benefit, advantage, or solution to occur or become more pronounced are not to be construed as critical, required, or essential features or elements of any or all the claims or the invention. The scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described exemplary embodiments that are known to those of ordinary skill in the art are expressly incorporated herein by reference and are intended to be encompassed by the present claims.

We claim:

1. A computer-implemented method for staging the movement of a plurality of dental objects, the method comprising:
   receiving, at a host computer, an electronic representation of each dental object of the plurality of dental objects in relation to one another;
   receiving, by the host computer, an electronic representation of a desired final position for each respective dental object; and
   determining, by the host computer, an order of movement for each respective dental object such that the dental objects avoid colliding with or obstructing each other on their respective routes from said initial position to said desired final position through at least one of staggering and round-tripping of at least one dental object.

2. The computer-implemented method of claim 1, wherein determining the order of movement, comprises:
   (a) determining a route each respective dental object will move to achieve its respective final position;
   (b) determining the distance each respective dental object will move to achieve its respective final position; and
   (c) determining a rate at which each respective dental object will move along its respective route.

3. The computer-implemented method of claim 2, further comprising:
   determining (a), (b), and (c) in relation to each of the other dental objects.

4. The computer-implemented method of claim 3, wherein determining (a), (b), and (c) in relation to each of the other dental objects step comprises adjusting at least one of the route and the rate of at least one dental object to avoid collision with at least one other dental object.

5. The computer-implemented method of claim 1, further comprising determining, by the host computer, an optimal number of stages for the order of movement of the dental objects.

6. The computer-implemented method of claim 5, wherein determining the optimal number of stages step comprises:
   determining a total distance each respective dental object will move;
   dividing the total distance for each dental object by its respective maximum speed to determine a number of movement stages for each dental object;
   determining a number of non-movement stages for each respective dental object;
   adding the number of movement stages to the number of non-movement stages for each dental object to determine a minimum number of stages for each respective dental object; and
   selecting the largest of the minimum number of stages.

7. The computer-implemented method of claim 1, wherein the determining the order of movement, comprises, ordering the movement of the dental objects to form an all-equal pattern.

8. The computer-implemented method of claim 1, wherein the determining the order of movement step comprises ordering the movement of the dental objects to form a V-shaped pattern.

9. The computer-implemented method of claim 1, wherein the determining the order of movement comprises: ordering the movement of the dental objects to form an A-shaped pattern.

10. The computer-implemented method of claim 1, wherein determining the order of movement step comprises ordering the movement of the dental objects to form an M-shaped pattern.

11. The computer-implemented method of claim 1, wherein, determining the order of movement step comprises ordering the movement of the dental objects to form a midline shift pattern.

12. The computer-implemented method of claim 1, wherein, determining the order of movement step comprises staggering the movement of at least two dental objects.

13. The computer-implemented method of claim 1, wherein determining the order of movement step comprises, round tripping at least one dental object.

14. The computer-implemented method of claim 1, wherein determining the order of movement step comprises, slowing the movement of at least one dental object.

15. A system for staging the movement of a plurality of dental objects, the system comprising:
   means for receiving an electronic representation of each dental object of the plurality of dental objects in relation to one another;
   means for receiving an electronic representation of a desired final position for each respective dental object; and
   means for determining an order of movement for each respective dental object such that the dental objects avoid colliding with each other on their respective routes from said initial position to said desired final position.

16. The system of claim 15, wherein the means for determining the order of movement comprises:
   (a) means for determining a route each respective dental object will move to achieve its respective final position;
   (b) means for determining the distance each respective dental object will move to achieve its respective final position; and
   (c) means for determining a rate at which each respective dental object will move along its respective route.

17. The system of claim 16, further comprising means for determining (a), (b), and (c) in relation to each of the other dental objects.

18. The system of claim 17, wherein the means for determining (a), (b), and (c) in relation to each of the other dental objects comprises means for adjusting at least one of the route and the rate of at least one dental object to avoid collision with at least one other dental object.

19. The system of claim 15, further comprising means for determining an optimal number of stages for the order of movement of the dental objects.

20. The system of claim 19, wherein the means for determining the optimal number of stages step comprises:
  means for determining a total distance each respective dental object will move;
  means for dividing the total distance for each dental object by its respective maximum speed to determine a number of movement stages for each dental object;
  means for determining a number of non-movement stages for each respective dental object;
  means for adding the number of movement stages to the number of non-movement stages for each dental object to determine a minimum number of stages for each respective dental object; and
  means for selecting the largest of the minimum number of stages.

21. The system of claim 15, wherein the means for determining the order of movement comprises means for ordering the movement of the dental objects in an all-equal pattern.

22. The system of claim 15, wherein the means for determining the order of movement comprises means for ordering the movement of the dental objects in a V-shaped pattern.

23. The system of claim 15, wherein the means for determining the order of movement comprises means for ordering the movement of the dental objects in an A-shaped pattern.

24. The system of claim 15, wherein the means for determining the order of movement comprises means for ordering the movement of the dental objects to form an M-shaped pattern.

25. The system of claim 15, wherein the means for determining the order of movement comprises means for ordering the movement of the dental objects in a mid-line shift pattern.

26. The system of claim 15, wherein the means for determining the order of movement comprises means for staggering the movement of at least two dental objects.

27. The system of claim 15, wherein the means for determining the order of movement comprises means for round tripping at least one dental object.

28. The system of claim 15, wherein the means for determining the order of movement comprises means for slowing the movement of at least one dental object.

29. A machine-readable medium having stored thereon a plurality of instructions for staging the movement of a plurality of dental objects, the plurality of instructions when executed by a processor, causing the processor to:
  receive an electronic representation of each dental object in relation to one another in an initial position;
  receive an electronic representation of a desired final position for each respective dental object; and
  determine an order of movement for each respective dental object such that the dental objects avoid colliding with each other on their respective routes from said initial position to said desired final position.

30. The machine-readable medium of claim 29, wherein the instructions causing the processor to determine the order of movement instructions further comprise instructions to:
  (a) determine a route each respective dental object will move to achieve its respective final position;
  (b) determine the distance each respective dental object will move to achieve its respective final position; and
  (c) determine a rate at which each respective dental object will move along its respective route.

31. The machine-readable medium of claim 30, further comprising instructions to:
  determine (a), (b), and (c) in relation to each of the other dental objects.

32. The machine-readable medium of claim 31, wherein the instructions to determine (a), (b), and (c) in relation to each of the other dental objects comprises instructions to adjust at least one of the route and the rate of at least one dental object to avoid collision with at least one other dental object.

33. The machine-readable medium of claim 29, further comprising instructions to determine an optimal number of stages for the order of movement of the dental objects.

34. The machine-readable medium of claim 33, wherein the instructions to determine the optimal number of stages comprise instructions to:
  determine a total distance each respective dental object will move;
  divide the total distance for each dental object by its respective maximum speed to determine a number of movement stages for each dental object;
  determine a number of non-movement stages for each respective dental object;
  add the number of movement stages to the number of non-movement stages for each dental object to determine a minimum number of stages for each respective dental object; and
  select the largest of the minimum number of stages.

35. The machine-readable medium of claim 29, wherein the instructions to determine the order of movement comprise instructions to order the movement of the dental objects to form an all-equal pattern.

36. The machine-readable medium of claim 29, wherein the instructions to determine the order of movement comprise instructions to order the movement of the dental objects to form a V-shaped pattern.

37. The machine-readable medium of claim 29, wherein the instructions to determine the order of movement, comprise instructions to order the movement of the dental objects to form an A-shaped pattern.

38. The machine-readable medium of claim 29, wherein the instructions to determine the order of movement comprise instructions to order the movement of the dental objects to form an M-shaped pattern.

39. The machine-readable medium of claim 29, wherein the instructions to determine the order of movement comprise instructions to order the movement of the dental objects a mid-line shift pattern.

40. The machine-readable medium of claim 29, wherein the instructions to determining the order of movement, comprise instructions to stagger the movement of at least two dental objects.

41. The machine-readable medium of claim 29, wherein the instructions to determine the order of movement comprise instructions to round-trip at least one dental object.

42. The machine-readable medium of claim 29, wherein the instructions to determine the order of movement comprise instructions to slow the movement of at least one dental object.

* * * * *